(12) United States Patent
Rossi et al.

(10) Patent No.: US 11,753,525 B2
(45) Date of Patent: Sep. 12, 2023

(54) NATURAL CRYSTALLINE COLORANT AND PROCESS FOR PRODUCTION

(71) Applicant: E. & J. Gallo Winery, Modesto, CA (US)

(72) Inventors: Joseph Rossi, Fresno, CA (US); Sundeep Kattamuri, Hyderabad (IN)

(73) Assignee: E. & J. Gallo Winery, Modesto, CA (US)

( * ) Notice: Subject to any disclaimer, the term of this patent is extended or adjusted under 35 U.S.C. 154(b) by 0 days.

(21) Appl. No.: 17/708,949

(22) Filed: Mar. 30, 2022

(65) Prior Publication Data
US 2022/0220282 A1    Jul. 14, 2022

Related U.S. Application Data

(60) Continuation of application No. 17/201,978, filed on Mar. 15, 2021, now Pat. No. 11,578,187, which is a (Continued)

(51) Int. Cl.
*C08K 5/3417*    (2006.01)
*A23L 5/42*    (2016.01)
(Continued)

(52) U.S. Cl.
CPC ............. *C08K 5/3417* (2013.01); *A23L 5/42* (2016.08); *A23L 5/44* (2016.08); *A23L 5/46* (2016.08); *B01D 1/065* (2013.01); *B01D 3/001* (2013.01); *B01D 9/0031* (2013.01); *B01D 11/0403* (2013.01); *B01D 11/0492* (2013.01); *B01D 15/08* (2013.01); *B01D 61/145* (2013.01); *B01D 61/58* (2013.01); *B01D 63/10* (2013.01); *B01D 71/68* (2013.01); *C08K 5/132* (2013.01); *C08K 5/1545* (2013.01); *C09B 61/00* (2013.01);
(Continued)

(58) Field of Classification Search
CPC . C08K 5/3417; A23L 5/46; A23L 5/44; A23L 5/42; B01D 1/065
See application file for complete search history.

(56) References Cited

U.S. PATENT DOCUMENTS 1,881,063 A    10/1932    Randolph
1,988,031 A    1/1935    Barnett
(Continued)

FOREIGN PATENT DOCUMENTS

CA    2987089 A1    12/2016
CA    3115497 A1    4/2020
(Continued)

OTHER PUBLICATIONS

Ayhan, Topuz et al; Influence of different drying methods of carotenoids and capsaicinoids of paprika (CV jalapeno) Food Chemistry, Elsevier LtD, NL, vol. 129, No. 3; Nat 5, 2011, pp. 860-865.
(Continued)

*Primary Examiner* — Sean E Conley
(74) *Attorney, Agent, or Firm* — Goodwin Procter LLP

(57) ABSTRACT

A crystalline pigment or colorant composition having high color intensity and/or low sugar content, and methods and processes of preparation. The composition may comprise purified fruit and/or vegetable color juices.

14 Claims, 10 Drawing Sheets

Related U.S. Application Data continuation of application No. 16/181,982, filed on Nov. 6, 2018, now Pat. No. 10,982,070, which is a division of application No. 15/449,828, filed on Mar. 3, 2017, now Pat. No. 10,214,630, which is a continuation of application No. 14/313,955, filed on Jun. 24, 2014, now Pat. No. 9,624,354, which is a division of application No. 13/536,578, filed on Jun. 28, 2012, now Pat. No. 8,790,717.

(60) Provisional application No. 61/503,557, filed on Jun. 30, 2011.

(51) Int. Cl.
| | | |
|---|---|---|
| *A23L 5/44* | (2016.01) | |
| *A23L 5/46* | (2016.01) | |
| *C08K 5/132* | (2006.01) | |
| *C08K 5/1545* | (2006.01) | |
| *C09B 61/00* | (2006.01) | |
| *C12P 7/06* | (2006.01) | |
| *B01D 1/06* | (2006.01) | |
| *B01D 3/00* | (2006.01) | |
| *B01D 9/00* | (2006.01) | |
| *B01D 11/04* | (2006.01) | |
| *B01D 15/08* | (2006.01) | |
| *B01D 61/14* | (2006.01) | |
| *B01D 61/58* | (2006.01) | |
| *B01D 63/10* | (2006.01) | |
| *B01D 71/68* | (2006.01) | |

(52) U.S. Cl.
CPC .............. *C12P 7/06* (2013.01); *A23V 2002/00* (2013.01); *B01D 2315/16* (2013.01); *B01D 2325/20* (2013.01); *Y02E 50/10* (2013.01)

(56) References Cited

U.S. PATENT DOCUMENTS

| | | |
|---|---|---|
| 2,134,906 A | 11/1938 | Byron |
| 2,235,559 A | 3/1941 | Mayer |
| 2,911,732 A | 11/1959 | Webb |
| 3,108,402 A | 10/1963 | Henry |
| 3,150,005 A | 9/1964 | Oleson |
| 3,151,950 A | 10/1964 | Newman |
| 3,206,866 A * | 9/1965 | McCabe .................. F26B 5/041 159/902 |
| 3,217,421 A | 11/1965 | Lowe |
| 3,228,113 A | 1/1966 | Fannon, Jr. |
| 3,250,315 A | 5/1966 | Osborne et al. |
| 3,258,467 A | 6/1966 | Anderson et al. |
| 3,266,559 A | 8/1966 | Osborne |
| 3,307,270 A | 3/1967 | Kruger |
| 3,436,791 A * | 4/1969 | Chambon ................. B01J 2/02 425/231 |
| 3,570,576 A | 3/1971 | Griffon |
| 3,641,681 A | 2/1972 | Brock |
| 3,805,316 A | 4/1974 | Sheppard |
| 3,915,691 A | 10/1975 | Sakagami et al. |
| 4,127,947 A | 12/1978 | Webb et al. |
| 4,152,842 A | 5/1979 | Laughlin |
| 4,259,063 A | 3/1981 | Spirin et al. |
| 4,306,358 A | 12/1981 | King, Jr. |
| 4,452,822 A | 6/1984 | Shrikhande |
| 4,631,837 A | 12/1986 | Magoon |
| 4,664,061 A | 5/1987 | Morioka et al. |
| 4,763,572 A | 8/1988 | Kuehl |
| 5,052,313 A | 10/1991 | Walker |
| 5,098,790 A | 3/1992 | Diemunsch et al. |
| 5,238,503 A | 8/1993 | Phenix et al. |
| 5,617,647 A | 4/1997 | Okane et al. |
| 5,632,097 A | 5/1997 | Snitchler et al. |
| 5,884,769 A | 3/1999 | Anderson |
| 6,047,484 A | 4/2000 | Bolland et al. |
| 6,112,677 A | 9/2000 | Kuntschar et al. |
| 6,195,913 B1 | 3/2001 | Canet et al. |
| 6,230,421 B1 | 5/2001 | Reed, Sr. et al. |
| 6,269,550 B1 | 8/2001 | Martin |
| 6,468,573 B1 | 10/2002 | Herrick et al. |
| 6,497,107 B2 | 12/2002 | Maisotsenko et al. |
| 6,539,645 B2 | 4/2003 | Savarese |
| 6,688,018 B2 | 2/2004 | Soucy |
| 6,742,277 B2 | 6/2004 | Sakurazawa |
| 6,990,748 B2 | 1/2006 | Magoon et al. |
| 6,990,751 B2 | 1/2006 | Riley et al. |
| 7,208,181 B1 | 4/2007 | King et al. |
| 7,211,413 B2 | 5/2007 | Matsumoto et al. |
| 7,325,331 B2 | 2/2008 | Luukkanen |
| 7,572,468 B1 | 8/2009 | Ishida et al. |
| 8,464,437 B1 | 6/2013 | Weisselberg |
| 8,826,558 B2 | 9/2014 | Priebe et al. |
| 8,889,054 B2 * | 11/2014 | Cakmak .................. B29C 39/14 264/171.1 |
| 8,984,763 B2 | 3/2015 | Savarese |
| 9,068,777 B2 | 6/2015 | Savarese |
| 9,829,249 B2 | 11/2017 | Tice |
| 9,863,704 B2 | 1/2018 | Vild |
| 10,335,720 B2 | 7/2019 | Pomerleau |
| 11,221,179 B2 | 1/2022 | Ortiz et al. |
| 2002/0055471 A1 | 5/2002 | Bailey et al. |
| 2002/0082459 A1 | 6/2002 | Bailey et al. |
| 2002/0095818 A1 | 7/2002 | Jain et al. |
| 2003/0041780 A1 | 3/2003 | Isager et al. |
| 2004/0191384 A1 | 9/2004 | Naik et al. |
| 2004/0194337 A1 | 10/2004 | Gasparini et al. |
| 2004/0231186 A1 | 11/2004 | Kolb et al. |
| 2005/0068774 A1 | 3/2005 | Pippa et al. |
| 2005/0115099 A1 | 6/2005 | Magoon et al. |
| 2005/0175720 A1 | 8/2005 | McKenzie |
| 2005/0181101 A1 | 8/2005 | Harada et al. |
| 2006/0272174 A1 | 12/2006 | Hartig |
| 2007/0082399 A1 | 4/2007 | Egorova-Zachernyuk |
| 2007/0110857 A1 | 5/2007 | Hartal et al. |
| 2007/0294911 A1 | 12/2007 | Wilson |
| 2008/0075824 A1 | 3/2008 | Biehl |
| 2008/0087168 A1 | 4/2008 | Wright et al. |
| 2008/0201978 A1 | 8/2008 | Hammer |
| 2008/0260915 A1 | 10/2008 | Alkayali |
| 2009/0226589 A1 | 9/2009 | Ferreira |
| 2009/0246315 A1 | 10/2009 | Barnekow et al. |
| 2010/0048957 A1 | 2/2010 | Kim |
| 2010/0145116 A1 | 6/2010 | Van Keulen et al. |
| 2012/0076904 A1 | 3/2012 | Sinha et al. |
| 2014/0202028 A1 | 7/2014 | De Santos Avila et al. |
| 2014/0259725 A1 | 9/2014 | Rossi et al. |
| 2017/0227288 A1 | 8/2017 | Pardo |
| 2018/0045462 A1 | 2/2018 | Baeghbali et al. |
| 2018/0156539 A1 | 6/2018 | Baudouin et al. |
| 2020/0132370 A1 | 4/2020 | Ortiz et al. |
| 2022/0090857 A1 | 3/2022 | Ortiz et al. |
| 2022/0228805 A1 | 7/2022 | Jolly |

FOREIGN PATENT DOCUMENTS

| | | |
|---|---|---|
| CN | 1323541 A | 11/2001 |
| CN | 1986539 A | 6/2007 |
| CN | 201184732 Y | 1/2009 |
| CN | 107388803 A | 11/2017 |
| EP | 0542669 A1 | 5/1993 |
| EP | 0695510 A1 | 2/1996 |
| EP | 2725925 B1 | 5/2014 |
| EP | 3369783 A1 | 9/2018 |
| FR | 2399467 A1 | 3/1979 |
| FR | 3037640 A1 | 12/2016 |
| GB | 499539 A | 1/1939 |
| GB | 554930 A | 7/1943 |
| GB | 570827 A | 7/1945 |
| GB | 785584 A | 10/1957 |
| JP | S57153702 A | 9/1982 |
| JP | S60248981 A | 12/1985 |
| JP | S61223481 A | 10/1986 |
| JP | H04209515 A | 7/1992 |

(56) References Cited

FOREIGN PATENT DOCUMENTS

| | | |
|---|---|---|
| JP | H1015358 A | 1/1998 |
| JP | H1151562 A | 2/1999 |
| JP | 2004293942 A | 10/2004 |
| JP | 2005082588 A | 3/2005 |
| JP | 2006506448 A | 2/2006 |
| JP | 2009508877 A | 3/2009 |
| JP | 2009531316 A | 9/2009 |
| JP | 2009531330 A | 9/2009 |
| JP | 2012145281 A | 8/2012 |
| JP | 5185098 B2 | 4/2013 |
| WO | WO-2002077105 A1 | 10/2002 |
| WO | WO-03079816 A1 | 10/2003 |
| WO | WO-2008004206 A2 | 1/2008 |
| WO | WO-2010139746 A2 | 12/2010 |
| WO | WO-2012/009469 A2 | 1/2012 |
| WO | WO-2013/003616 A1 | 1/2013 |
| WO | WO-2014145952 A1 | 9/2014 |
| WO | WO-2016203170 A1 | 12/2016 |
| WO | WO-2020086957 A1 | 4/2020 |
| WO | WO-2021022298 A2 | 2/2021 |

OTHER PUBLICATIONS

Bolland: Refractance Window Food Drying System Delivers Quality Product Efficiently, Jul. 21, 2000; Retrieved from the Internet: URL:https://www.foodonline.com/doc/refractance- window-food-drying-system-deliver-0001, retrieved on Jun. 29, 2018.
Buskov et al, Separation of chlorophylls and their degradation products using pack/ed column supercritical fluid chromatography (SFC) HRC, Journal of High Resolution Chromatography (1999), vol. 22, No. 6, pp. 339-342.
Careri, Supercritical fluid extraction for liquid chromatographic determination of carotenoids in Spirulina Pacifica algae: a chemometric approach. Journal of chromatography. A, (Mar. 30, 2001) vol. 912, No. 1, pp. 61-71 (Year: 2001).
Clarke, Phillip, Refractance Window TM Down Under, Jan. 1, 2004, pp. 813-820, XP055489211, Retrieved from the internet: URL: http://files.gwdryer.com/dryer-technology-comparison.pdf— Retrieved on Jun. 29, 2018, Chapter: "The Refractance Windows Process"; p. 814.
European Search Report dated Jul. 6, 2018 in corresponding EP Application No. EP18154793 filed on Feb. 1, 2018.
Hossain, Concentration of anthocyanin pigments in blackcurrant pomace by ultrafiltration. Food Australia (2003), vol. 55, No. 6, pp. 263-266.
Ide et al, Ultrafiltration with spiral wound membrane technology. Official Proceedings—International Water Conference (1990), 51st, 362-73.
International Search Report dated Jul. 12, 2012 in corresponding PCT Application No. PCT/US2012/046687, filed Jun. 28, 2012, inventor(s) Rossi, Joseph et al.
Ling, Guanting, Antioxidant food and health, Chemical Industry Publishing, first edition, pp. 231-232, 2004.
Lionetto, Effect of the daily ingestion of a purified anthocyanin extract from grape skin on rat serum antioxidant capacity. Physiological research/ Academia Scientiarum Bohemoslovaca, (2011) vol. 60, No. 4, pp. 637-645. Electronic Publication Date: May 16, 2011.
Nindo et al, Refractance window dehydration technology: a novel contact drying method. Drying Technology (2007), 25(1-3), 37-48 (Year: 2007).
Office Action dated Aug. 21, 2018 by the Japanese Patent Office (JPO)in corresponding Japanese application No. 2017-126421 filed on Jun. 28, 2017.
Office Action dated Jul. 24, 2018 by the Japanese Patent Office (JPO) in corresponding Japanese application No. 2017-126401 filed on Jun. 8, 2017.
Office Action dated Sep. 5, 2018 by Canadian Intellectual Property Office (CIPO) in corresponding Canadian application No. 2,840,213 filed on Jun. 12, 2012.
Ravindra, Antioxidant activity of the anthocyanin from carrot (*Daucus carota*) callus culture. International iournal of food sciences and nutrition, (Sep. 2003) vol. 54, No. 5, pp. 349-355.
Skerget et al, Separation of paprika components using dense $CO_2$. Acta Alimentaria (Budapest) (1998), vol. 27, No. 2, pp. 149-160.
Zhao, Yunxia et al., Research on the purification and antioxidant activity of mulberry red pigment, Science and Technology of Food Industry, vol. 29, pp. 250-253 2008.
Zimmer, Membrane filtration: practical experience with juice pretreatment and filtration of coloured iuices. Fruit Processing (2007), 17(3), 153-158.
Thao, et al., "Methods to characterize the structure of food powders," Bioscience, Biotechnology, and Biochemistry, vol. 81, Issue 4, Apr. 3, 2017.
Caparino, et al., "Effect of drying methods on the physical properties and microstructures of mango (*Philippine 'Carabao'* var.) powder," Journal of Food Engineering 111 (2012).
Pavan, "Effects of freeze drying, refractive window drying and hot-air drying on the quality parameter of Acai," Master Thesis, University of Illinois, 2010, available at: http://hdl.handle.net/2142/15990.
Sunlite Flat Multiwall Polycarbonate Sheet. Palram., (Mar. 4, 2013), URL: https://web.archive.org/Web/20130304050051/http://www.palram.com/SUNLITE, (Jul. 7, 2014), XP055281823.
International Search Report and Written Opinion for International Patent Application No. PCT/US2014/030810, dated Aug. 20, 2014 (8 Pages).
International Search Report and Written Opinion for International Patent Application No. PCT/US2019/058055, dated Jan. 10, 2020 (8 pages).
Shao, J; Zydney, A, "Optimization of Ultrafiltration/Diafiltration Processes for Partially Bound Impurities", *Biotechnology and Bioengineering*, 87/3, pp. 286-292, Jul. 7, 2004.

* cited by examiner

NATURAL CRYSTALLINE COLORANT AND PROCESS FOR PRODUCTION

CROSS-REFERENCE TO RELATED APPLICATIONS

The present application claims priority to and is a continuation of U.S. application Ser. No. 17/201,978 entitled "NATURAL CRYSTALLINE COLORANT AND PROCESS FOR PRODUCTION" filed on Mar. 15, 2021, which claims priority to and is a continuation of U.S. application Ser. No. 16/181,982 entitled "NATURAL CRYSTALLINE COLORANT AND PROCESS FOR PRODUCTION" filed on Nov. 6, 2018, now U.S. Pat. No. 10,982,070 issued on Apr. 20, 2021, which claims priority to and is a divisional of U.S. application Ser. No. 15/449,828 entitled "NATURAL CRYSTALLINE COLORANT AND PROCESS FOR PRODUCTION" filed on Mar. 3, 2017, now U.S. Pat. No. 10,214,630, issued on Feb. 26, 2019, which claims priority to and is a continuation of U.S. application Ser. No. 14/313,955 entitled "NATURAL CRYSTALLINE COLORANT AND PROCESS FOR PRODUCTION" filed on Jun. 24, 2014, now U.S. Pat. No. 9,624,354, issued on Apr. 18, 2017, which is a divisional of and claims priority to U.S. application Ser. No. 13/536,578 entitled "NATURAL CRYSTALLINE COLORANT AND PROCESS FOR PRODUCTION" filed on Jun. 28, 2012 now U.S. Pat. No. 8,790,717, issued on Jul. 29, 2014, which claims the benefit of and priority to U.S. Provisional Patent Application No. 61/503,557 entitled "NATURAL CRYSTALLINE COLORANT AND PROCESS FOR PRODUCTION" filed on Jun. 30, 2011, the entire contents of each of which are hereby incorporated by reference.

FIELD

The present disclosure relates in general to purified natural color pigments and colorants and processes for preparing and processing the pigments and colorants.

BACKGROUND

Natural colors and dyes are primarily derived from pigments that are found in plants including fruits, flowers and vegetables. Based on their chemical composition, natural plant-sourced pigments can be classified into structural groups including, but not limited to, anthocyanins, betalains, carotenoids, curcumin, carminic acid and derivatives, chlorophylls and their derivatives, etc. Carotenoids include, but are not limited to, β-carotene, α-carotene, apocarotenal, lycopene, bixin, norbixin, canthaxanthin, and zeaxanthin. Chlorophyll and chlorophyllin derivatives include, but are not limited to, copper complexes. In another non-limiting embodiment, the pigment may be complexed with a metal ion such as, but not limited to, copper.

One objective of the manufacturing industry is to concentrate the pigmented portion of plants to provide a more concentrated natural colorant that can be added to various food, drug, and cosmetic products. These concentrated colorants are produced by removing other compounds through separation processes.

Natural colorants are often recovered from fruit and vegetable juices which are high in sugar relative to the fraction of pigmented compounds. These sugar-based colors are typically concentrated to remove water and are used as a concentrate with greater than 60 percent sugar on a dry weight basis and low pigment levels. It will be appreciated that the concentrate may have higher or lower percentage sugar on a dry weight basis depending on the fruit or vegetable. Low color content liquids are expensive to store (often requiring refrigeration), are subject to degradation over time, have a high calorie to color contribution ratio in food or beverage applications due to high sugar content, and/or may impart undesired sensory characteristics.

The industry has provided two different forms of these natural colorants from fruit and vegetable juices, namely liquids and powders. Sugar-based colors are often difficult to dry and typically require a carrier such as maltodextrin or micro-crystalline cellulose to compensate for the hygroscopic character of the sugar.

Further, since the liquids that are subjected to drying are typically at about 50% w/w to 80% w/w water content, there are very few technologies available to efficiently dry such products. The most common technology available for drying liquids that have a low concentration of soluble solids is spray drying.

Unfortunately, spray drying has some disadvantages when it comes to handling of the dried product. Typical problems include, but are not limited to, significant deterioration of the product quality due to the high temperature and pressure that the liquid is subjected to during drying, the formation of amorphous particles with low bulk density due to the rapid rate of drying in micronized droplets, and poor water dissolution or wettability characteristics as well as hygroscopic tendencies due to the presence of sugars in an amorphous rather than crystalline state, making the powders prone to lumping or caking. Furthermore, successful spray drying of a fruit or vegetable concentrate with high sugar content typically requires the presence of a carrier, thereby weakening the color concentration and dosage efficiency of the finished product.

Another objective of the manufacturing industry is to substantially reduce the sugar fraction of the standard fruit- and vegetable-based color concentrates to produce a more concentrated natural color with lower caloric density that can also be dried to yield a product with improved storage and handling characteristics. Purified colors are typically produced by removing the non-pigment components of fruit and vegetable juices and extracts, thereby significantly enriching the material in the color compounds. Purified colors, containing low concentrations of sugar, can be dried using a broad range of drying processes including spray, drum, refractive window, and freeze driers. The present process provides combinations of purification and drying technology to produce concentrated natural color that can be dried without carriers. The concentrated natural colors described herein have a high color intensity and/or improved sensory, stability, and handling characteristics relative to other dry colors known to the industry.

The foregoing examples of the related art and limitations related therewith are intended to be illustrative and not exclusive. Other limitations of the related art will become apparent to those of skill in the art upon a reading of the specification and a study of the drawings.

SUMMARY

The following aspects and embodiments thereof described and illustrated below are meant to be exemplary and illustrative, not limiting in scope.

The present disclosure relates to unique dried colorants obtained from natural sources including plants, such as fruits and vegetables, and algae. In embodiments, the colorants are obtained from fruit and/or vegetable juices or juice concentrates and/or extracts. In further embodiments, the colorants are obtained from red grape juice and/or purple carrot juice. The process of producing the dried colorant includes, briefly, purifying the color pigments using various purification technologies and subsequently removing water using low temperature drying methods. This novel combination of purification technologies and low temperature drying produces a unique natural colorant that is high in color and/or low in sugar. In embodiments, the colorants described herein exhibit superior storage stability and/or handling characteristics including, but not limited to density, flowability, water dispersion and/or hygroscopicity.

In one aspect, a natural colorant composition comprising a crystalline pigment or mixture of pigments derived from plants and/or algae are contemplated. In an embodiment, the composition has a color intensity that is higher than the color intensity of raw juice or an unpurified pigment or composition. In a further embodiment, the composition of the above aspect and/or embodiment has decreased sugar on a dry weight basis as compared to raw juice or an unpurified pigment composition. In another embodiment, the composition of the above aspect and/or embodiments contains less than about 5-20% sugar on a dry weight basis. In a further embodiment, the composition of the above aspect and/or embodiments has a total sugar content of less than about 20% of dry weight. In yet another embodiment, the composition of the above aspect and/or embodiments has a color intensity greater than about 40,000 color units. In another embodiment, the pigment of the above aspect and/or embodiments is a red grape anthocyanin and the composition has a color intensity of about 40,000-55,000 color units. In a further embodiment, the pigment of the above aspect and/or embodiments is a purple carrot anthocyanin and the composition has a color intensity of about 90,000-125,000 color units. In an additional embodiment, the pigment of the above aspect and/or embodiments is selected from the group consisting of anthocyanins, carotenoids, betalains, curcumin, carminic acid, carminic acid derivatives, chlorophyll, and chlorophyll derivatives.

In another aspect, a process for producing a purified, crystalline natural pigment is contemplated. The process comprises (a) purifying a juice or extract containing pigments by removing at least a portion of non-pigment compounds to produce a purified pigment; and (b) drying the purified pigment. In an embodiment, the purified pigment is crystalline and has an increased color intensity and/or decreased sugar content on a dry weight basis compared to raw juice. In another embodiment, the pigment of the above aspect and/or embodiments is selected from the group consisting of anthocyanins, carotenoids, betalains, curcumin, carminic acid, carminic acid derivatives, chlorophyll, and/or chlorophyll derivatives. In a further embodiment, the step of purifying in the process of the above aspect and/or embodiments comprises ultrafiltration and diafiltration across a polymeric membrane system. In yet another embodiment, the polymeric membrane system of the above aspect and/or embodiments comprises polyethersulfone (PES) spiral ultrafiltration membranes. In a further embodiment, the PES spiral ultrafiltration membranes of the above aspect and/or embodiments have a nominal molecular weight cutoff of about 5000 daltons. In yet another embodiment, the step of purifying of the above aspect and/or embodiments comprises circulating the juice or extract through a membrane system comprising (a) filtering the juice or extract through a membrane system; (b) recovering a retentate; (c) reconstituting the retentate; and (d) repeating steps (a) to (b) until the retentate reaches a desired color strength on a dry weight basis. In an additional embodiment, step of purifying of the above aspect and/or embodiments comprises adsorption/desorption chromatography. In another embodiment, purifying of the above aspect and/or embodiments comprises a fermentation process. In a further embodiment, purifying of the above aspect and/or embodiments comprises a subcritical or a supercritical fluid extraction process. In yet another embodiment, the step of drying of the above aspect and/or embodiments is accomplished with a refractive window drier. In a further embodiment, the step of drying of the above aspect and/or embodiments comprises freeze-drying. In another embodiment, the process of the above aspect and/or embodiments further comprises milling the dried product.

In a further embodiment, a composition formed by the process of any of the above aspect or embodiments, alone or in any combination is contemplated.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

Figure 1:
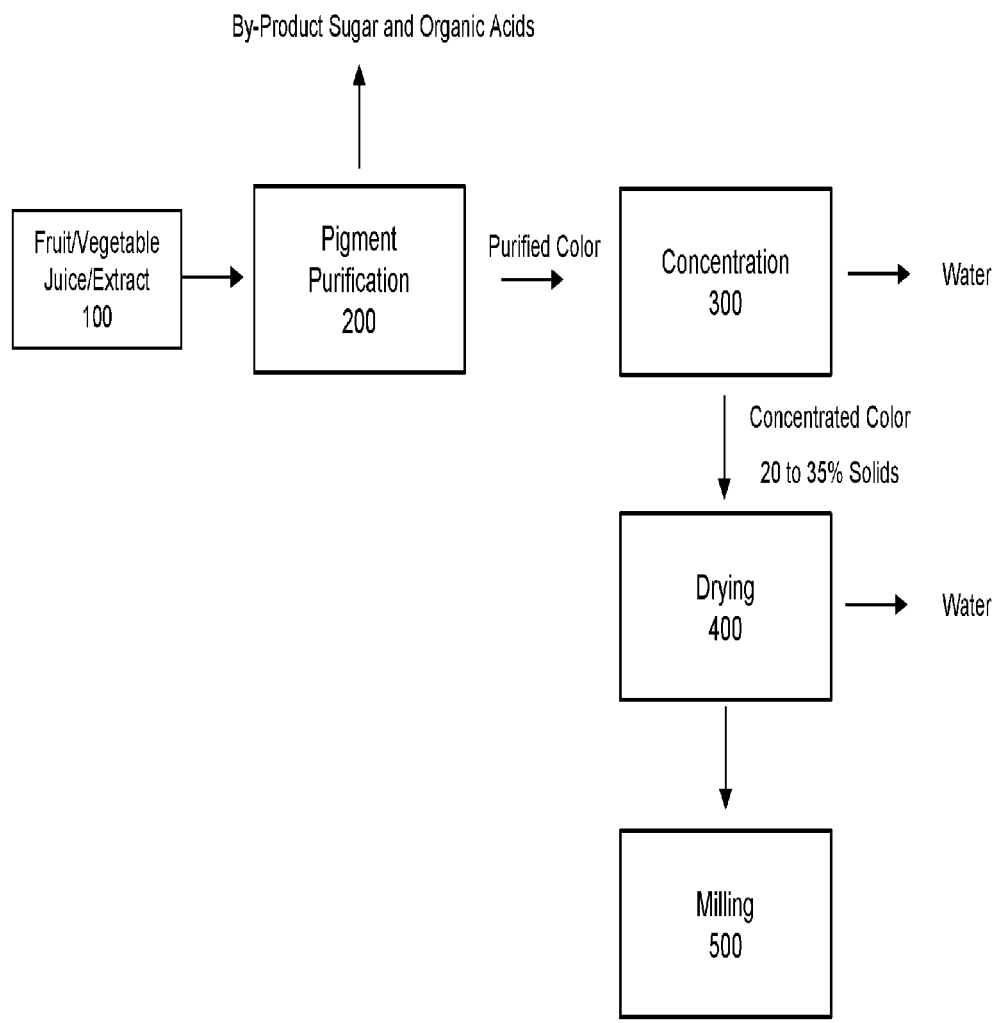
FIG. 1 is a flow chart illustrating an exemplary process for purifying and drying natural fruit and vegetable based pigments, according to one embodiment.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details.

The terms "colorant" and "pigment" as used herein refer to any substance used to modify the color of an object by changing its spectral transmittance or its spectral reflectance. "Colorant" and "pigment" as used herein generally refer to colorants and pigments obtained from natural sources including, but not limited to plants and algae. "Colorant" and "pigment" are used interchangeably herein.

A "concentrate" as used herein refers to a juice or extract that has had at least some of the water removed.

"Juice" as used herein refers to the liquid obtained from a fruit, vegetable or other plant. Juice may also refer to liquid obtained from algae. As used herein, "juice" includes concentrate and extract. "Raw juice" as used herein refers to juice that has not been purified.

"Increased color intensity" refers to an increase in color intensity as compared to the color intensity of raw juice and/or unpurified pigment compositions.

"Decreased sugar content" refers to a decrease in sugar content on a dry weight basis as compared to raw juice and/or unpurified pigment.

Concentrations, amounts, pH values, etc., are often presented herein in a range format. The description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as 10-15% should be considered to have specifically disclosed subranges such as 10-11%, 10-12%, 10-13%, 10-14%, 11-12%, 11-13%, etc.

Method of Preparing Colorants

In one aspect, a method of preparing a colorant is described. It will be appreciated that the present method may be used to prepare a pigment or colorant and the terms are used interchangeably herein. Briefly, the process includes (i) optional reconstitution and pasteurization of a juice concentrate or extract, (ii) purification of the juice concentrate or extract such as by ultrafiltration and diafiltration, (iii) concentration of the purified juice concentrate or extract such as by falling film evaporation, (iv) drying, and (v) milling. While prior dry colorants in the food industry are spray-dried powders, the present dry colorants use low temperature drying, such as with refractive window drying technology or freeze drying, to produce crystalline solid color additives that are 100% natural, high in antioxidants, extremely concentrated in color, and/or completely water soluble.

FIG. 1 illustrates exemplary process steps to produce the unique crystalline product described above. Fruit and/or vegetable juice and/or extract 100 is typically, but not always, reconstituted (diluted) before purification. In one non-limiting embodiment, concentrate at about 68° Brix is reconstituted to about 18-22° Brix. In an embodiment, concentrate is reconstituted with approximately 3 parts water to one part concentrate. Once reconstituted, the juice may be more susceptible to fermentation from any yeast cells that might be present in the starting material. Since the juice will remain at a low solids level throughout all of the subsequent liquid processing, it may optionally be pasteurized immediately to enhance microbial stability from the start of the process. The juice or extract may be pasteurized according to methods known in the art. According to one non-limiting embodiment, the juice or extract is pasteurized by heating to about 185° F. for about 30 seconds and then immediately cooling to about 55° F. The juice or extract is typically, but not always, pasteurized into a jacketed tank that becomes the feed tank for subsequent membrane filtration. All tanks used in the process may be jacketed and/or temperature controlled using, for example, food-grade propylene glycol as the refrigerant.

The juice/extract is then purified 200. By increasing the concentration of pigment relative to sugar and organic acids, the color-enriched liquid, under the proper drying conditions, can be converted efficiently into a crystalline form with superior properties, such as handling properties.

The juice/extract may be purified according to any suitable methods known in the art. In one preferred embodiment, purification 200 is achieved through the use of ultrafiltration and diafiltration across polymeric membranes. Ultrafiltration (and subsequent iterations of diafiltration) produces a retentate that is enriched in pigments such as anthocyanin pigments or carotenoid pigments while simultaneously depleted in the sugars and acids that more easily permeate through the membrane. Removal of sugar increases the color concentration or color intensity on a dry weight basis while also creating a product with superior storage and handling properties relative to other colorants known to the industry. Alternative methods of color purification include, but are not limited to, column chromatography with adsorbent resins, fermentation, and extraction including, but not limited to, subcritical fluid extraction, supercritical fluid extraction, and/or solvent extraction.

In the case of pigment purification using membrane separation, purified pigments, low in sugar and organic acids, are concentrated 300 by removing water using evaporation. Depending on the membrane process, it may be possible to dry the purified product directly without concentration. Once a liquid of suitable composition and solids content has been prepared, the liquid is dried 400 under proper conditions effective to create a product with the described format and properties. These conditions allow suitable rates of water removal to achieve crystallization of the solids while avoiding significant thermal damage to the color compounds.

Figure 2:
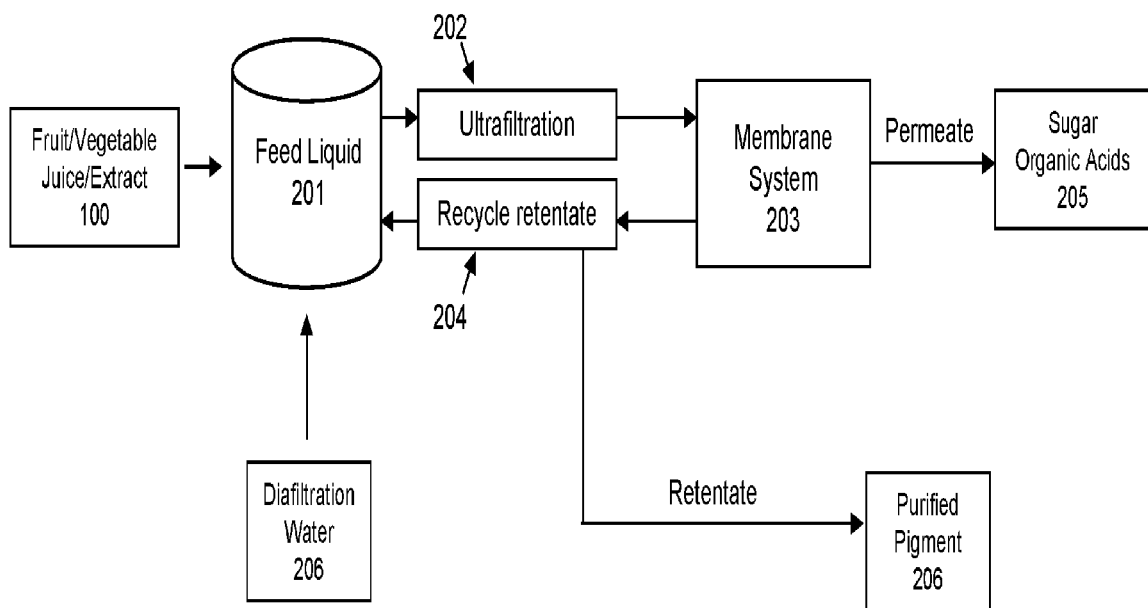
FIG. 2 is a flow chart illustrating an exemplary process for purifying a colorant using ultrafiltration and diafiltration, according to one embodiment.

FIG. 2 illustrates an exemplary process for purifying color pigments using ultrafiltration and diafiltration to remove natural sugars and other low molecular weight dissolved solids such as organic acids from the retentate, according to one embodiment. In this embodiment, the feed 100 to the membrane system is preferably a fruit or vegetable juice/extract of less than about 40° Brix, and preferably between about 12-22° Brix. In one embodiment, the membrane system 203 comprises polymeric membranes as known in the art. The membrane system 203 used in one embodiment is composed of polyethersulfone (PES) with a molecular weight cutoff in the range of about 5,000-10,000 Daltons, such as those manufactured by Koch Membrane Systems or Hydranautics. Membranes of this type provide rejection characteristics suitable for creating a permeate stream 205 that is enriched in sugar and acids and a retentate stream 204 increasingly enriched in pigment compounds such as anthocyanins and polyphenols relative to the concentration of sugar and acid. In another exemplary embodiment, a system of PES spiral ultrafiltration membranes with a nominal molecular weight cutoff of about 5,000 Daltons is used. Ultrafiltration 202 may be performed over any operating temperature and pressure ranges that avoid damage to the membranes and provide sufficient cross flow as specified by the membrane manufacturer. However, in the present embodiment, maintaining temperatures below about 70° F. or more preferably below about 40° F., maintains product quality by slowing pigment color degradation kinetics. Retentate 204 from the membrane system 203 is returned to the feed tank 201 and circulated back through the ultrafiltration membranes 202 until a limiting viscosity and flux is reached, typically at a retentate solids concentration of about 20-25% by weight. Further purification may then continue by adding water to the retentate 206 and concentrating again by circulating through the membrane 203 up to a limiting solids concentration. Diafiltration 206 sequences are repeated until the desired pigment purity is achieved in the retentate. The retentate, according to one embodiment, contains pigment concentrations greater than about 45,000 color units on a dry weight basis compared to the base extract/juice of about 3,000 color units on a dry weight basis.

The diafiltration step may be modified by adding water 206 at a rate approximately equal to the rate of permeate 205 leaving the system, thereby performing a continuous diafiltration until the desired retentate composition is achieved.

After each concentration, retentate samples may be analyzed for residual sugar and color strength on a dry weight basis (color strength as liquid+percent solids by weight). Once the retentate reaches a color strength on a dry basis that produces the product within the desired specifications, the product is concentrated 300. Due to the natural variation in the composition of the feed material for this process, the amount of diafiltration required can vary, typically from about 2-4 diafiltrations.

As a non-limiting example of a batch size, a feed tank of 5,000 gallons of reconstituted, pasteurized juice at about 18-20° Brix will be circulated through the membrane system with the retentate recycled back to the feed tank until the tank reaches a solids level of about 30° Brix (at which point the decrease in flux usually prohibits further concentration). This results in approximately a fourfold reduction in volume of the feed liquid, leaving about 1,500 gallons of retentate. Because this initial concentration may not increase the ratio of pigments such as anthocyanin pigment molecules to sugar enough to achieve a targeted color strength, the retentate may undergo several diafiltrations to reach a sufficient dissolved solids composition. According to one embodiment, for each diafiltration, the retentate is reconstituted with a 1:1 volumetric ratio of water to concentrate and the about 3,000 gallons of reconstituted material is circulated through the membrane system and concentrated back to the original retentate volume of about 1,500 gallons.

In a non-limiting embodiment, throughout the ultrafiltration and diafiltration process, the permeate may pass through a small surge tank attached to the membrane skid and be pumped out to a 20K gallon permeate accumulation tank in the plant cellar where it is concentrated and used in concentrate blends.

After achieving the desired color intensity on a dry weight basis by adjusting the ratio of pigment to sugars, membrane processing ends and the retentate liquid may be further concentrated in solids without adjusting the solids composition.

Figure 5:
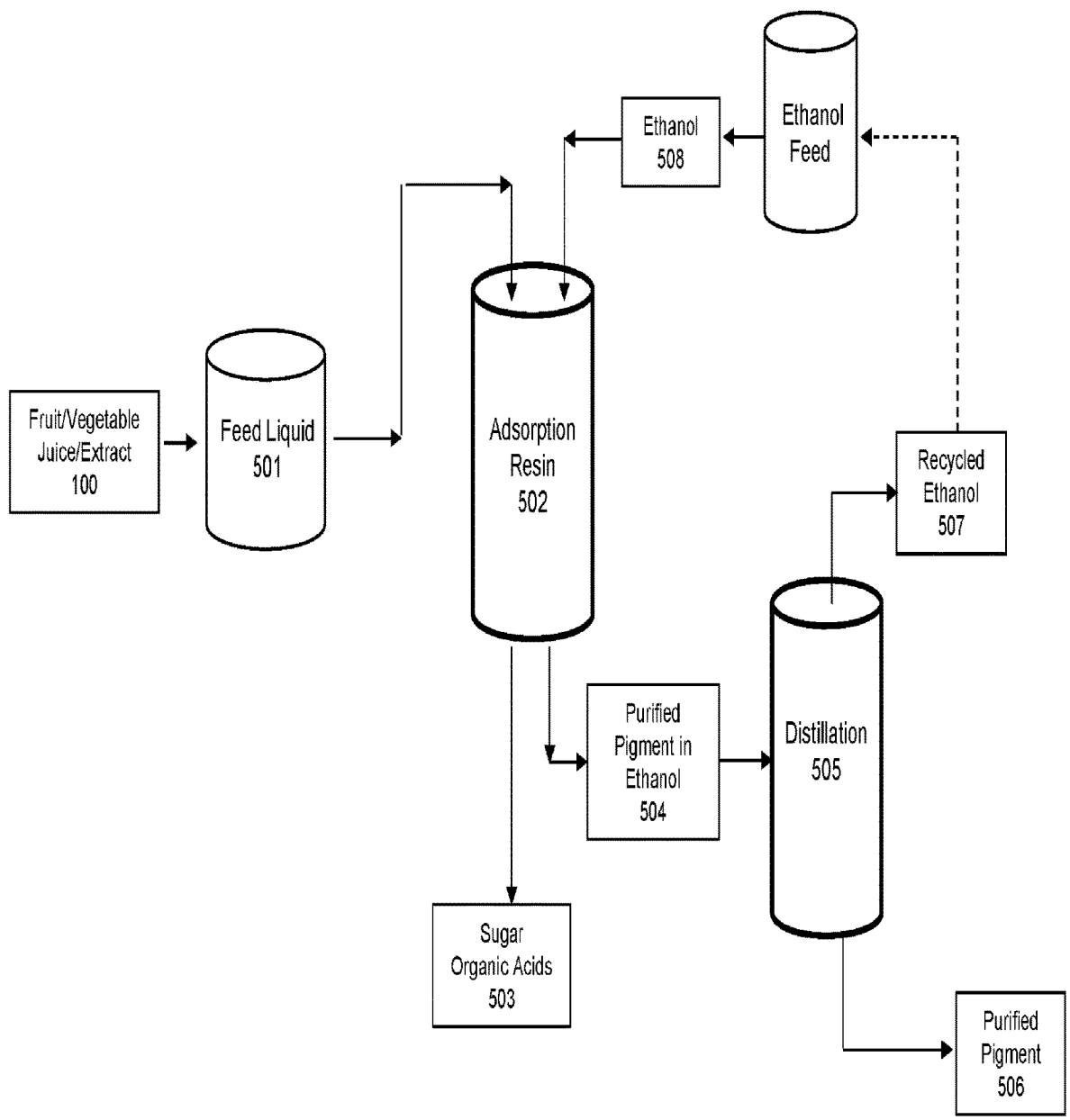
FIG. 5 is a flow chart illustrating an exemplary process for purifying color using adsorption resin separation technology, according to one embodiment.

Pigment purification can also be achieved using adsorption resin separation technology. In this embodiment, shown in FIG. 5, a water-based fruit or vegetable juice/extract 100 is passed (feed liquid 501) through a packed bed of adsorbent resins 502. The pigment compounds are preferentially adsorbed on the resins relative to other dissolved solids such as sugar and acids 503. The adsorbed pigments are subsequently recovered from the resin using an ethanol/water eluent 508 of varying composition. The purified, pigment rich eluate 504 is distilled 505 to recover ethanol 507. The alcohol-free, high purity pigment 506 is concentrated according to the processes noted in FIG. 3.

Figure 6:
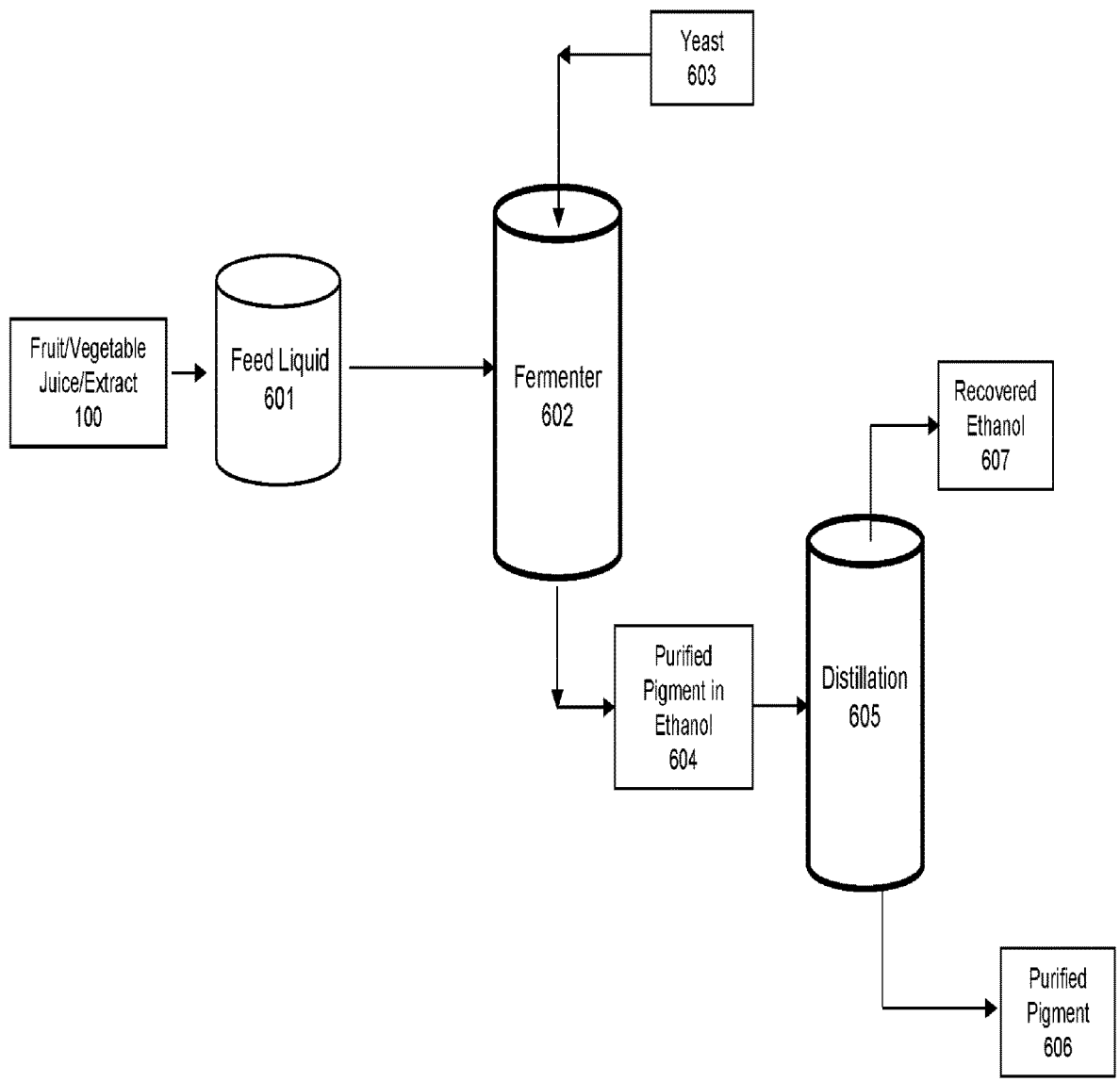
FIG. 6 is a flow chart illustrating an exemplary process for purifying color using fermentation technology, according to one embodiment.

In another embodiment, pigment purification can be achieved using fermentation to convert the free sugar to alcohol, and subsequently recovering the alcohol using conventional distillation processes. In this embodiment, shown in FIG. 6, the fruit/vegetable sugar from the fruit/vegetable juice/extract 100 (feed liquid 601) is fermented to alcohol using active yeast 603 at appropriate temperature (about 50° to 100° F.) in a suitable fermenter 602. It will be appreciated that other temperature ranges may be suitable for fermentation as known to those of skill in the art. The fermented by-product 604, comprised of about 8 to 25 percent alcohol, is distilled 605 to recover the ethanol 607 leaving purified color pigments 606. The alcohol-free liquid is subsequently concentrated by removing water according to the methods outlined in FIG. 3.

Figure 7:
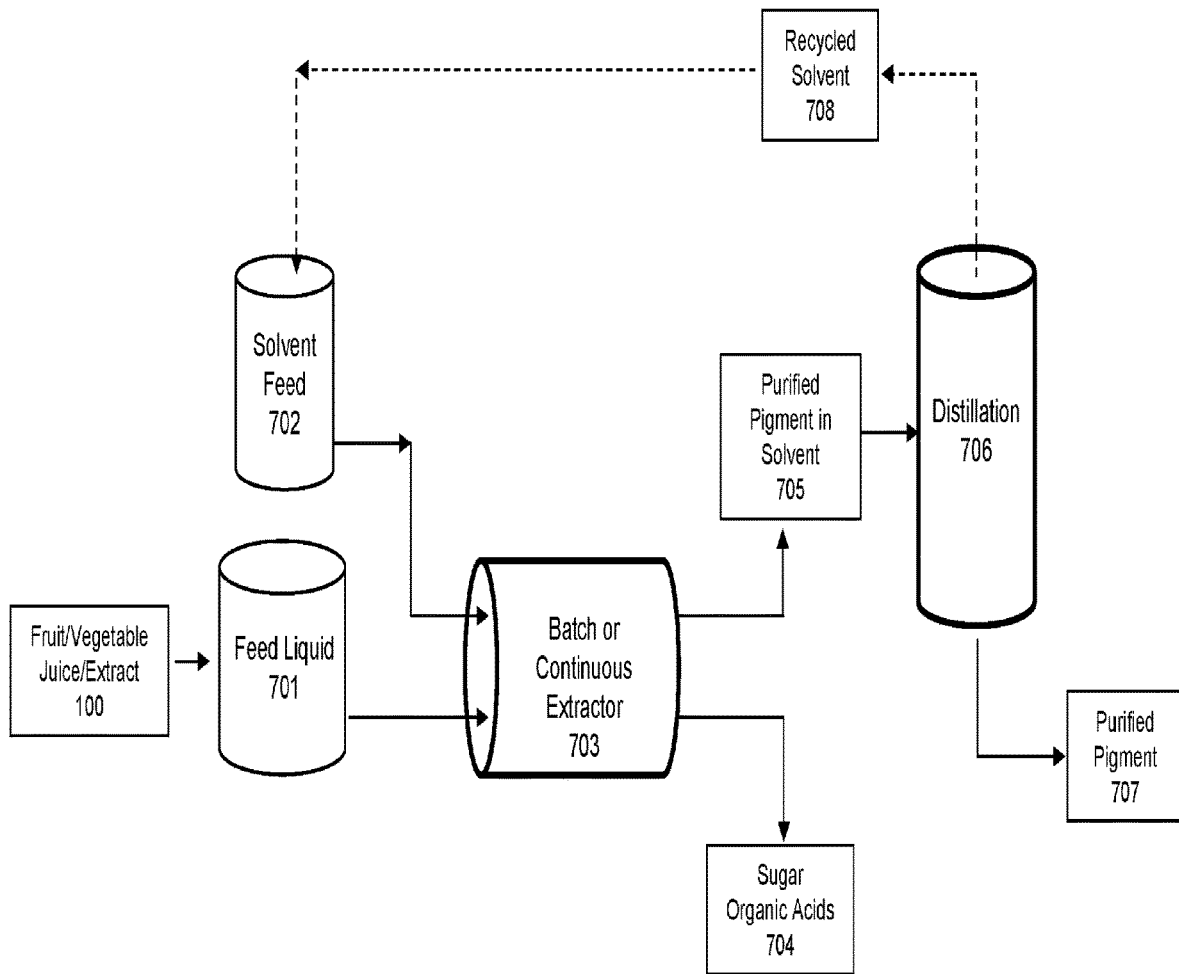
FIG. 7 is a flow chart illustrating an exemplary process for purifying color using solvent extraction technology, according to one embodiment.

In yet another embodiment, pigment purification is achieved using supercritical fluid or solvent-solvent extraction processes. In this embodiment, shown in FIG. 7, water-based fruit/vegetable juice/extract 100 (feed liquid 701) is contacted with a non-polar, non-water miscible extract liquid (such as hexane) or solvent 702 which preferentially absorbs the color compounds. The absorption process is repeated to yield an extract fraction rich in color compounds 705 and a fraction rich in carbohydrates and/or other non-colored components 704. A batch or continuous extractor 703 may be used to recover and concentrate the color. The extract solvent 705 is subsequently distilled 706 to recover the solvent for re-use 708, yielding a solvent-free, pigment-rich water-based liquid 707, which is subsequently concentrated by removing water according to the methods outlined in FIG. 3.

Figure 3:
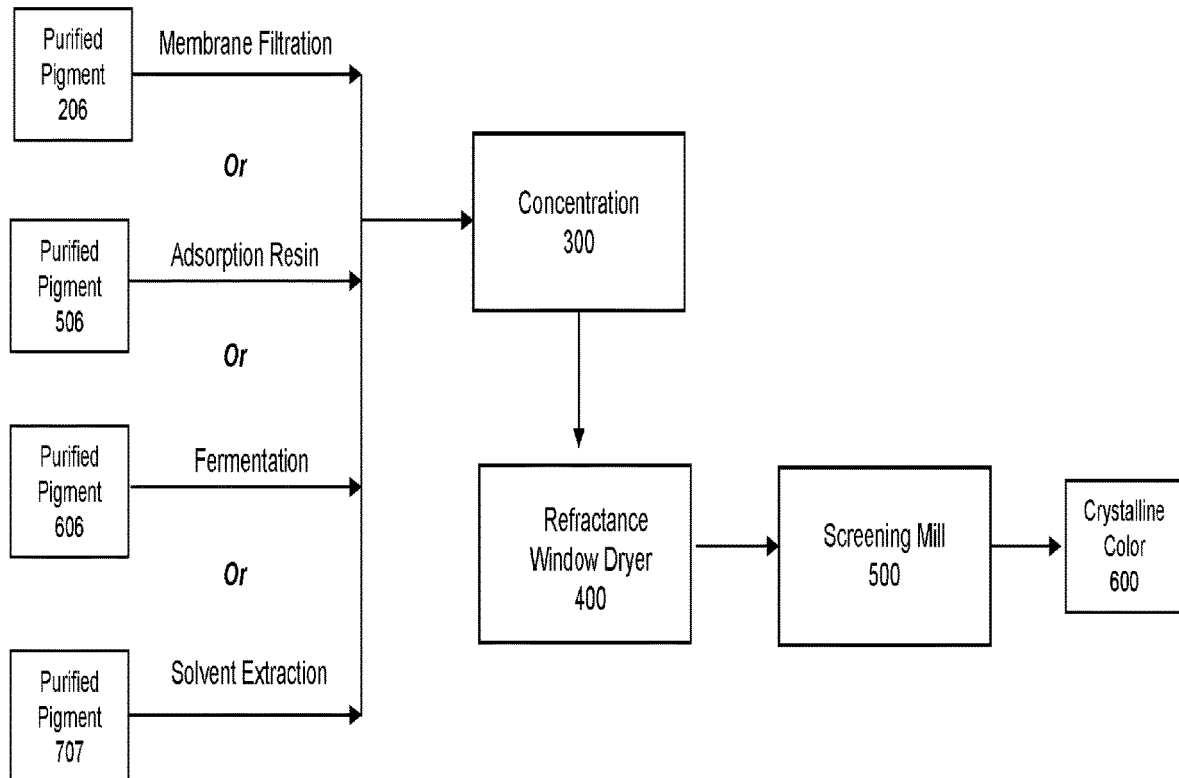
FIG. 3 is a flow chart illustrating an exemplary process for concentrating purified color liquid, drying, and milling, according to one embodiment.

FIG. 3 illustrates an exemplary process of concentrating 300 and drying 400 a purified color liquid using a refractive window dryer in an exemplary embodiment. The dried crystalline material is then milled 500 to produce a powder form with a consistent particle size range. Purified liquid can be produced using membrane filtration such as ultrafiltration/diafiltration, adsorption resin, fermentation, solvent extraction and/or supercritical fluid extraction technologies. Depending on the solids content in the purified liquid, it may be necessary to concentrate the solids to 20-35% by weight prior to drying.

Concentration 300 of the purified liquid color may be performed by feeding the final retentate from the previous step to a falling film evaporator, in one embodiment. Other types of evaporators, such as a forced circulation evaporator or plate evaporator may also be used.

In one non-limiting embodiment, the retentate is concentrated with a falling film evaporator prior to drying. One exemplary falling film evaporator is a small (single effect) falling film evaporator. In one embodiment using a falling film evaporator, a final solids content of about 15-20% by weight and about 25-30° Brix, the retentate is circulated through the evaporator until the solids concentration of the feed tank reaches about 25-30% solids by weight or about 40-45° Brix. This degree of concentration results in a volume reduction of approximately 45% and takes approximately 12 hours, according to one embodiment. The resulting liquid is then ready as feed material for drying, such as with a refractive window dryer. The liquid may additionally be pasteurized and packaged into mobile metal drums so that it can be stored without spoilage and can be transported in small units as needed.

Because the final concentrated liquid fed to the dryer still may not be at a shelf-stable solids concentration of concentrate (which could require concentration up to 68+° Brix), and is fed to the dryer at a rate of about 9-12 gallons per hour with some drying embodiments, an optional additional pasteurization step may be warranted at the end of liquid processing. This pasteurization step may kill any yeast cells that may have been introduced during processing before the liquid is stored and/or gradually fed to the dryer. Any method of pasteurization known in the art may be used. An exemplary method of pasteurization includes heating the liquid about 185° F. for about 30 seconds and cooling the liquid to about 55° F. into a surge tank. From this surge tank, the liquid may be immediately pumped to a barrel filler where it is injected, without exposure to air, into bags that line the barrels (e.g., 54-gallon metal barrels). According to one embodiment, barrels of finished liquid feed material are stored at approximately 40-50° F. The barrels may be brought to the dryer in groups (up to four for one pallet), where they are gradually depleted one at a time.

Purifying natural pigments ensures that the final dried product exhibits superior shelf stability and handling characteristics including density, flowability, water dispersion, and hygroscopicity. Purified color extracts have improved drying characteristics, and hence can be dried using a variety of standard drying techniques including spray, drum, belt, and atmospheric/vacuum tray drying. These techniques can subject the pigments to excessive high temperatures or residence time, resulting in color deterioration and/or adverse sensory impact. These drying techniques may also produce varying crystalline morphology with associated differences in quality or material handling characteristics. To prepare a crystalline product with superior quality, handling, and/or dissolution characteristics, the color concentrate must be dried slowly, as is the case for refractive and freeze drying, to allow formation of large crystal lattices, including crystallization of any residual sugar. In one embodiment, the present process uses a refractive window dryer that significantly reduces the temperature requirements for effective drying and the time of exposure to elevated temperatures. Spray drying and drum drying, in contrast, operate at higher temperatures to accomplish drying over a very short time and leaves components in an amorphous state. Freeze drying can also be used to produce large crystal lattices provided the base material is purified prior to drying.

After concentration, the liquid is dried to produce a crystalline solid pigment. In one embodiment, as shown in FIG. 3, the liquid may then be applied to a refractive window dryer 400 to remove most of the remaining water and produce a crystalline solid of less than about 8% moisture. The dryer 400 comprises a long tunnel, typically formed from stainless steel. Liquid product passes through tunnel as a thin layer spread across the top surface of a thin plastic conveyor belt 403. In the drying process, hot water circulates through shallow heating trays underneath the conveyor belt and heats the liquid layer, according to one embodiment. Thermal energy from the hot water is transmitted through the conveyor belt by means of conduction and radiation. In one embodiment, the hot water is at a temperature of up to about 210° F. It will be appreciated that the water may be any temperature suitable to heat the liquid layer to a desired temperature. Air blowers continuously sweep water vapor away from the thin layer surface to maximize the rate of water evaporation. The combination of evaporative cooling and limited heat conductivity of the plastic belt keep the thin liquid layer from reaching the temperatures of the hot water in the heating trays, which could negatively impact product quality. The product leaves the tunnel as a dried solid product layer which may be removed by a sharp plastic edge placed in contact with the belt at the end of the dryer. Contact with this edge causes the layer of dried product to break off into thin crystalline pieces of varying size.

The solid product exits the dryer in forms that can be described as sheets, flakes, or granules of varying particle size. These particles may then be milled through a screening mill 500, or other suitable particle size reduction equipment such as an impact mill, to produce particles in a desired size range. The desired particle size range may be determined by specific industry applications. In the embodiment where the pigments are prepared as a food colorant, the desired particle size consists of no less than about 90% of total particle size between about 50-425 µm for purposes of optimizing handling characteristics and standardizing bulk density. In other embodiments, about 90% of total particle size is less than about 100-200 µm, less than about 100-250 µm, less than about 100-300 µm, less than about 100-400 µm, less than about 200-250 µm, less than about 200-300 µm, less than about 250-300 µm, less than about 200-400 µm, or less than about 250-400 µm.

In one embodiment, the concentrated liquid feed material 300 passes through a dryer such as a refractive window dryer to remove water and produce a crystalline solid of less than about 8% moisture by weight. In other embodiments, the crystalline solid has less than about 5-10% moisture by weight.

In one non-limiting embodiment, the present disclosure concerns unique dry colors made from red grape juice concentrate and purple carrot juice concentrate. A particular embodiment is a crystalline red colorant from grapes with at least about 40,000 color units. In other embodiments, the crystalline red colorant has about 40,000-55,000 color units, about 42,000-55,000 color units, about 45,000-55,000 color units, about 40,000-50,000 color units, about 42,000-50,000 color units, about 45,000-50,000 color units. In further embodiments, the crystalline red colorant has greater than about 40,000 color units, greater than about 42,000 color units, greater than about 45,000 color units, greater than about 50,000 color units, or greater than about 55,000 color units. Another particular embodiment is a crystalline purple colorant from carrots with at least about 90,000 color units. In other embodiments, the crystalline purple colorant has about 85,000-130,000 color units, about 85,000-125,000 color units, about 90,000-130,000 color units, about 90,000-125,000 color units, about 95,000-130,000 color units, about 95,000-125,000 color units. about 100,000-130,000 color units, and about 100,000-125,000 color units. In further embodiments, the crystalline purple colorant has greater than about 85,000 color units, greater than about 90,000 color units, greater than about 95,000 color units, greater than about 100,000 color units, greater than about 125,000 color units, and greater than about 130,000 color units.

Figure 4A:
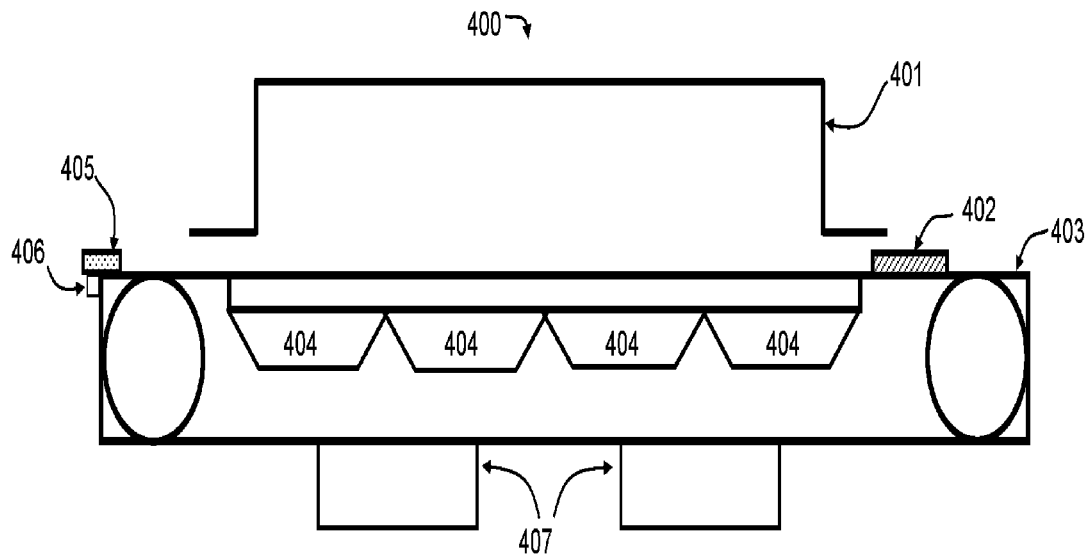
FIG. 4A is a side view illustration of a refractive window drier, according to one embodiment.
Figure 4B:
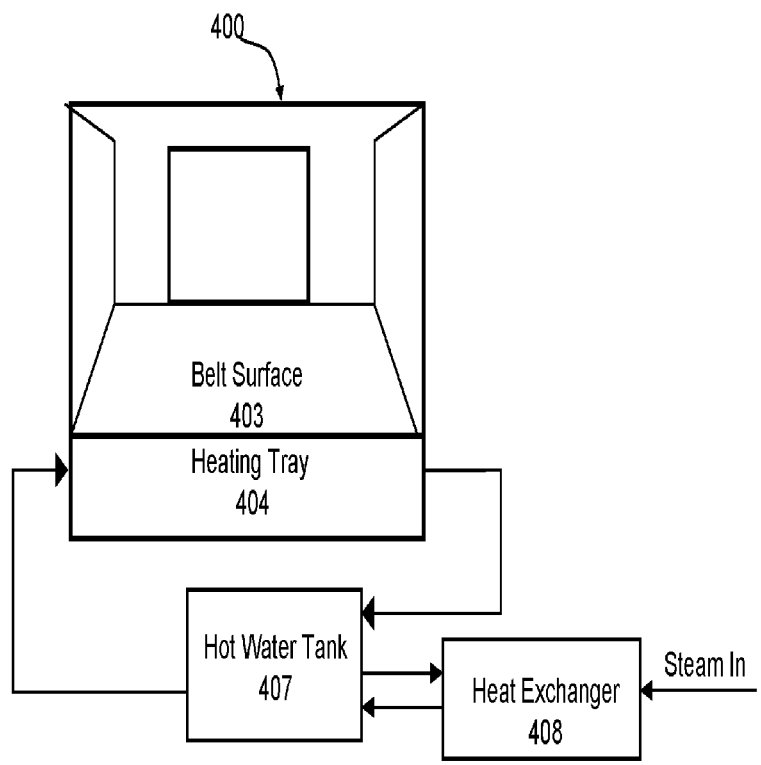
FIG. 4B is a cross-sectional view illustrating a refractive window drier, according to one embodiment.

FIG. 4A and FIG. 4B illustrates the side view and cross-sectional view of an exemplary refractive window dryer 400 respectively. The dryer 400 comprises a long tunnel 401, typically formed from stainless steel, suitable for rapid water evaporation. Liquid product passes through tunnel 401 as a thin layer 402 spread across the top surface of a thin plastic conveyor belt 403.

In one non-limiting embodiment, liquid colorant is applied to the belt using an air pump with a suction hose inserted into a feed barrel, which pumps liquid from the barrel through a filter, such as a 75 micron in-line filter, and into a small feed balance tank. The air pump is typically controlled by the level in the feed balance tank. Valves on feed spout(s) drain product onto an applicator tray, forming a thin layer on the moving surface of the belt.

Hot water circulates through shallow heating trays 404 underneath the conveyor belt 403 and heats the liquid layer 402, according to one embodiment. Thermal energy from the hot water is transmitted through the conveyor belt 403 by means of conduction and radiation. In one embodiment, the hot water is at a temperature of up to about 210° F. It will be appreciated that the water may be any temperature suitable to heat the liquid layer 402 to a desired temperature.

Air blowers continuously sweep water vapor away from the thin layer surface 402 to maximize the rate of water evaporation. The combination of evaporative cooling and limited heat conductivity of the plastic belt keep the thin liquid layer surface 402 from reaching the temperatures of the hot water in the heating trays 404, which could negatively impact product quality.

The product leaves the tunnel 401 as a dried solid product layer 405 which may be removed by a sharp plastic edge 406 placed in contact with the belt 403 at the bullnose end of the dryer. Contact with this edge causes the layer of dried product to break off into thin crystalline pieces of varying size. In one embodiment, the crystalline product falls off the end of the belt for collection. In an embodiment, plastic bags placed inside plastic barrels and supported by a mobile stainless steel frame are placed to collect the crystalline produce from the belt.

Soft water may be used for the water in the heating trays under the belt to avoid staining and deposits on the stainless steel. The water is typically held in tanks underneath the belt. In one embodiment, each tank is connected to and circulated through a heat exchanger that uses steam to reach and maintain an adjustable set point temperature.

Figure 8:
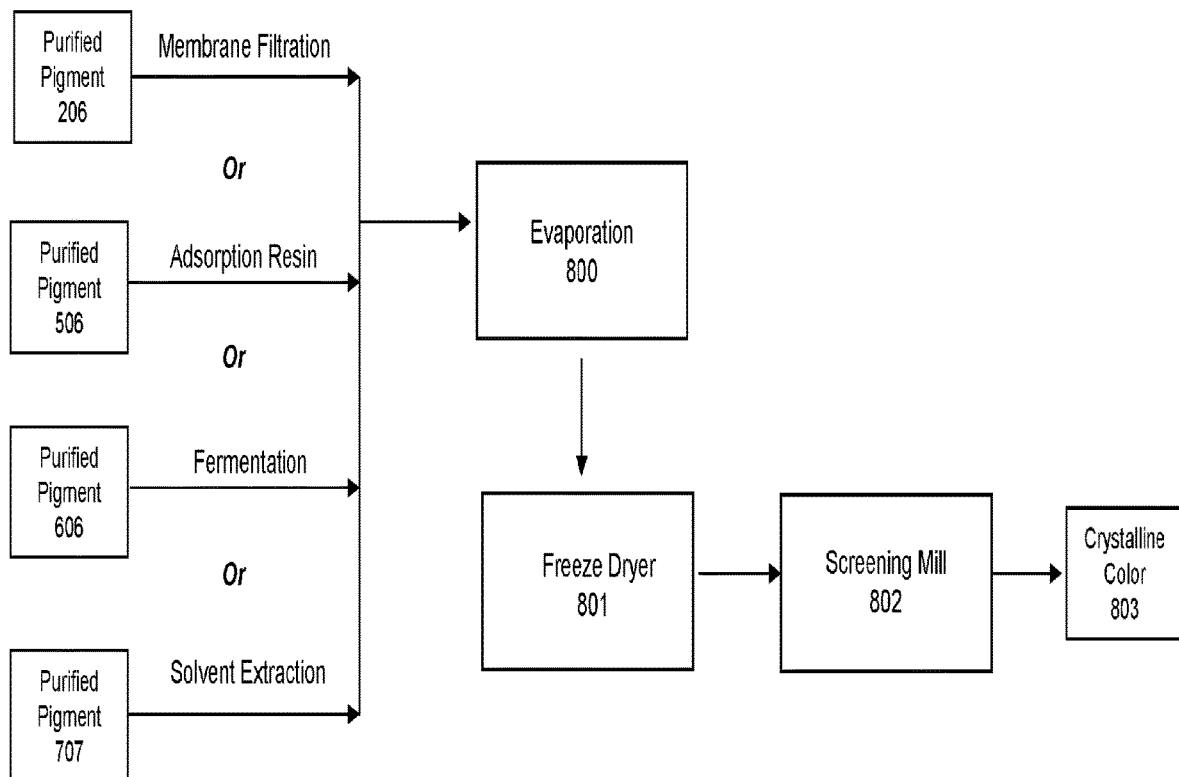
FIG. 8 is a flow chart illustrating an exemplary process for drying purified color using freeze-dry technology, according to one embodiment.

In another embodiment, the purified, liquid concentrate is dried using vacuum, freeze-drying processes to produce a dry powder with large crystalline structure exhibiting superior color stability, and/or color handling characteristics. In this embodiment, illustrated in FIG. 8, the purified liquid is placed in a freeze dryer 801 vacuum chamber. Air and water vapor is removed from the chamber under vacuum until the liquid in the trays is frozen. The frozen trays are then indirectly heated using an external source (i.e. steam, hot water, electricity) with the trays maintained under vacuum. Residual water is sublimed from the frozen material until moisture levels are below about 7 percent. The water sublimation step is performed at plate temperatures ranging from about 40° C. to 100° C. for a period of about 8 to 24 hours depending on the water content and composition of the pigment. Once the water is sublimed, the trays are removed from the vacuum chamber and the dry crystals are recovered as granules of varying size. The granules are milled through a screening mill 802, or other size reduction equipment such as impact mills as known in the art, to produce particles in a desired size range 803. The milling process produces a more consistent particle size and a higher packing density for better storage and/or shipping efficiency.

Crystalline Colorants/Pigments

In another aspect, a crystalline pigment or colorant is described. Preferably, the crystalline pigment or colorant is derived from natural plant or algae sources. The novel combination of purification technologies and drying produces a unique natural colorant, high in color and/or low in sugar that exhibits superior shelf stability and/or handling characteristics, including density, flowability, water dispersion and/or less hygroscopic character. As such, the present crystalline pigment or colorant overcomes some of the basic problems that the industry has been dealing with when using dry natural colorants.

In embodiments, derivatives and/or modifications of the crystalline pigment are contemplated. Modifications include, but are not limited to, co-pigmentation, saponification, complexing, and/or flaking. The pigments may be modified and then formulated into a colorant composition.

As seen in FIGS. 9A-9D, the present crystalline pigments are crystalline rather than amorphous. The present natural dry colorant is not spray dried and therefore is not amorphous in nature with low bulk density and does not require additives to enable drying or to make it less hygroscopic. Instead, the present natural dry colorant is dried using a milder drying technique, including, but not limited to drying with a refractive window dryer, or freeze-dryer.

The crystalline colorant or pigment may be produced from any suitable plant or algae producing desired pigments. In embodiments, the pigments consist of anthocyanins, carotenoids, curcumin, betalains, carminic acid and derivatives, and/or chlorophyll and derivatives. Carotenoids include, but are not limited to, β-carotene, α-carotene, apocarotenal, lycopene, bixin, norbixin, canthaxanthin, and zeaxanthin. Chlorophyll and chlorophyllin derivatives include, but are not limited to, copper complexes. In another non-limiting embodiment, the pigment may be complexed with a metal ion such as, but not limited to, copper. In non-limiting embodiments, the crystalline colorant or pigment is obtained from grapes or carrots. It will be appreciated that pigment compositions may include one or more crystalline pigments.

The present purified natural dry colorant is produced using a milder drying technique that yields a crystalline color that is non-hygroscopic. This purified crystalline color has excellent dispersability and dissolution characteristics due to its non-hygroscopic nature and does not require agglomeration and granulation to improve dissolution characteristics.

When purifying fruit and vegetable pigment juice and extracts, the composition of the sugar component is reduced from about 70% to 95% on a dry weight basis to about 10 to 20% on dry basis, according to one embodiment. In other embodiments, the sugar component is reduced to less than 10%, to less than 15%, to less than 20%, to 15-20%, to 10-15% on a dry basis. In further embodiments, crystalline pigments described herein have about 5-20% total sugar on a dry basis. In other embodiments, crystalline pigments have about 5-10% total sugar on a dry basis, about 5-15% total sugar on a dry basis, about 10-20% total sugar on a dry basis, about 10-15% total sugar on a dry basis, or about 15-20% total sugar on a dry basis. Reducing the concentration of sugar relative to total dried solids also concentrates the pigmented portion to about 7 to 15 times the original concentration on a dry weight basis, according to one embodiment. In embodiments, the pigmented portion is concentrated to about 7-10 times or 10-15 times the original concentration on a dry weight basis. There are several techniques for purifying the colorants, including ultrafiltration/diafiltration, adsorption resin, solvent extraction, fermentation, and super critical or sub critical fluid extractions.

As noted above, the crystalline colorant or pigments are high in color. Table 1 contrasts the color intensity of purified 10%, 20%, 25%, 50%, 75%, 100%, 150%, 200% increase in color intensity or more.

The ranges of values for residual sugar and color intensity are provided for illustration purposes only and represent nominal purification levels achievable using membrane purification processes. Lower residual sugar levels (down to less than 1 percent) are possible using additional or different membrane filtration and/or different purification processes including fermentation, adsorption resins, and solvent extraction.

TABLE 1

Purified Pigment Color Intensity for Extracts, Purified Concentrate, and Purified Powder

| Fruit/ Vegetable Pigment | Type | Sugar | Moisture | Color (520 nm) | Sugars on Dry Basis | Color Strength on Dry Basis |
|---|---|---|---|---|---|---|
| Grape | Raw Fruit Juice Concentrate | 55-60% | 30-40% | 1,800-2,200 | 90-95% | 2,800-3,500 |
| Grape | Purified Juice Concentrate | 3-7% | 65-80% | 12,000-16,000 | 10-20% | 40,000-55,000 |
| Grape | Purified Pigment Crystal Powder | 10-20% | 5-7% | 35,000-50,000 | 10-20% | 40,000-55,000 |
| Carrot | Raw Vegetable Juice Concentrate | 40-50% | 30-40% | 9,000-12,000 | 70-80% | 12,000-20,000 |
| Carrot | Purified Juice Concentrate | 3-7% | 65-80% | 30,000-40,000 | 5-20% | 90,000-125,000 |
| Carrot | Purified Pigment Crystal Powder | 5-20% | 5-7% | 85,000-120,000 | 5-20% | 90,000-125,000 | grape and carrot pigments to standard sugar-based natural colors. Color strength measurement for Table 1 is:

$$\frac{\text{Absorbance at 520 nm (1 cm pathlength)}}{\text{Grams of Sample per 100 ml Buffer Solution (pH 3.2)}} \times 2000.$$

As shown, the typical color intensity of unpurified fruit and vegetable juice concentrates is 2,000 to 12,000 color units. Purified pigments exhibited a color intensity of about 40,000 to 55,000 color units for grape anthocyanins, and about 90,000 to 125,000 color units for purple carrot anthocyanins. In an embodiment, the purified pigments have a color intensity of greater than about 40,000 color units for grape anthocyanins. In another embodiment, the purified pigments have a color intensity of greater than about 90,000 color units for purple carrot anthocyanins. In an embodiment, the color value is equal to:

$$\frac{\text{Absorbance at 520 nm (1 cm pathlength)}}{\text{Grams of Sample per 100 ml Buffer Solution (pH 3.2)}} \times 2000.$$

In a further embodiment, the purified pigments exhibit an increased color intensity as compared to raw juice and/or to unpurified pigments or pigment compositions. In non-limiting embodiments, increased color intensity refers to at least about 5-200% increase in color intensity. In further embodiments, increased color intensity refers to at least about 5%, As seen from Table 1, the purified pigment powder had significantly increased color as compared to the raw fruit extract/concentrate. As also seen from Table 1, the purified pigment powder had reduced sugar content as compared to the raw fruit extract/concentrate. The grape pigment had at least 4 times less sugar than the raw fruit extract/concentrate and the carrot pigment had at least 2.8 times less sugar. The purified crystal red grape pigment had 13-17 times stronger color strength on a dry basis than the unpurified grape juice concentrate. The purified crystal purple carrot pigment had 6-9 times stronger color strength on a dry basis than the unpurified purple carrot juice concentrate. In embodiments, the purified crystal pigment has 5-20 times stronger color strength on a dry basis as compared to an unpurified juice concentrate. In further embodiments, the purified crystal pigment has 5-10 times, 5-15 times, 10-15 times, or 10-20 times stronger color strength on a dry basis as compared to an unpurified juice concentrate.

The data shown in Table 1 reflects the use of membrane filtration to purify the natural pigment. Inherent in membrane filtration is a practical lower limit for sugar content based on the amount of diafiltration required and the decreasing yield of purified color with increased diafiltration. Other purification methods, such as fermentation or adsorption resins, can potentially achieve lower sugar content and hence higher relative purification. It will be appreciated that lower sugar content and higher color purity may be obtained with other purification methods.

Table 2 summarizes the differences in physical characteristics among refractive window, freeze, and spray dried powders produced from the same purified grape anthocyanin pigment. As shown, the refractive window and freeze dried crystals exhibit markedly different photomicroscopy, particle size distribution, and particle density compared to spray dried powder.

TABLE 2

Physical Characteristics for Purified Grape Pigments

| Parameter | Unit of Measure | Drying Method | | |
|---|---|---|---|---|
| | | Refractive Window | Freeze | Spray |
| Photomicroscopy | | Angular, glassy, micro-pores | Angular, glassy | Spherical, glassy |
| Particle Size distribution[1,2] | | | | |
| D10 | um | 47 | 54 | 9 |
| D50 | um | 123 | 142 | 19 |
| D90 | um | 277 | 287 | 38 |
| Density | | | | |
| Bulk | (g/cm$^3$) | 0.62 to 0.70 | 0.28 to 0.37 | 0.24 to 0.44 |
| Particle | (g/cm$^3$) | 1.5 | 1.4 | 0.9 |

[1]0.5 bar dispersion pressure
[2]The terms D10, D50, and D90 refer to the particle sizes at which 10%, 50%, and 90% of the sample is smaller.
Notes:
The moisture content of the refractive window and spray dried products were 3.0% and 3.5%, respectively.

Figure 10A:
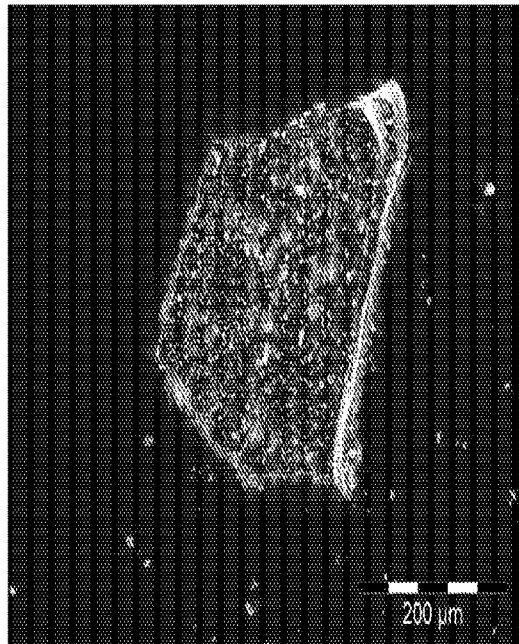
FIGS. 10A-10D are microscopy images of FIGS. 9A-9D at 20× magnification.
Figure 10B:

As seen from FIGS. 9A-9B and 10A-10B, refractive window and freeze dried powders exhibit a glassy and angular crystal, reflecting relatively slow crystal growth compared to spray dried powders. Refractive window crystals further exhibit micropores within the base crystal structure (FIG. 10A). The angular, glassy morphology of the refractive window and freeze-dried crystals provide the superior physical and flowability characteristics as further discussed below.

Figure 9A:
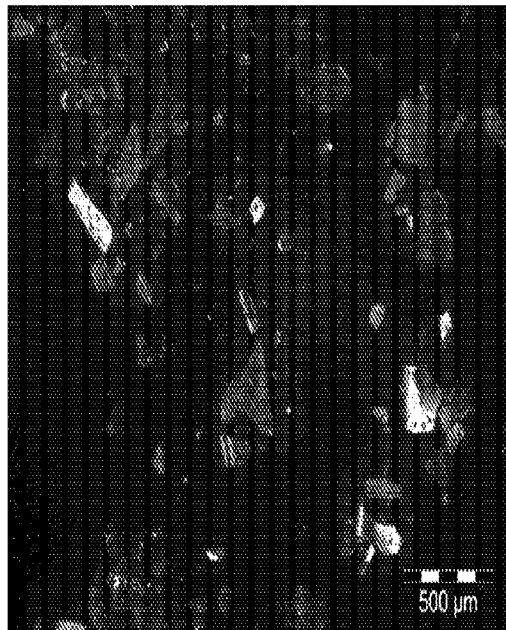
FIGS. 9A-9D are microscopy images at 5× magnification of purified grape pigments that are refractive window dried (FIG. 9A), freeze-dried (FIG. 9B), spray dried (FIG. 9C), and drum dried (FIG. 9D).
Figure 9B:
Figure 9C:
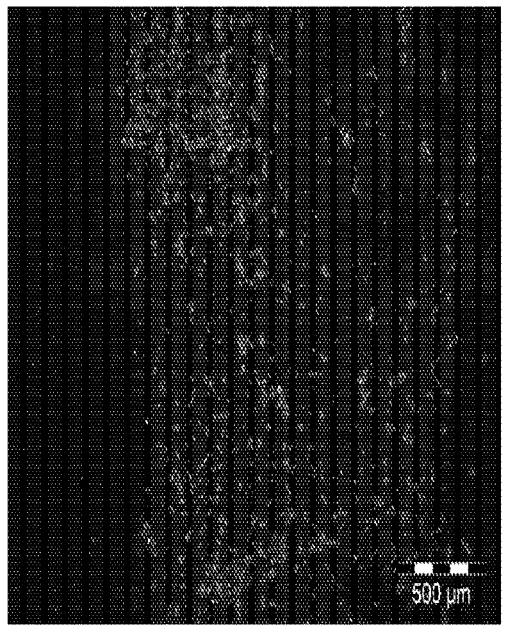
Figure 9D:
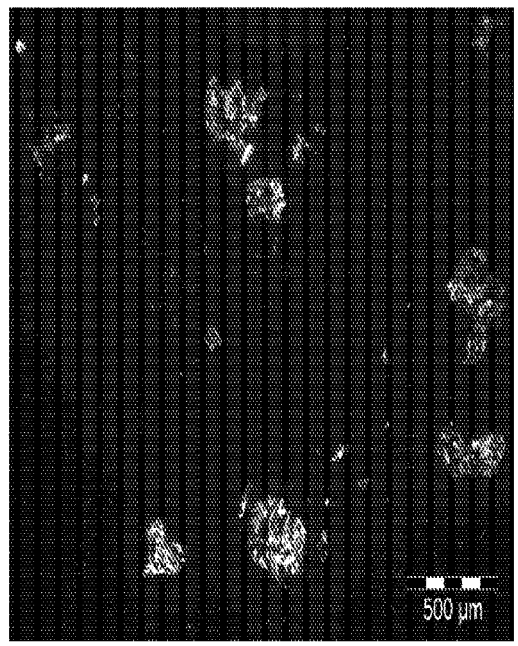
Figure 10C:
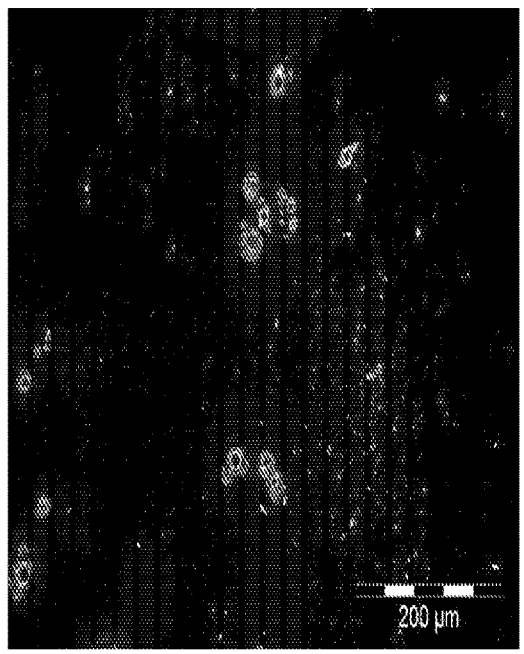
Figure 10D:
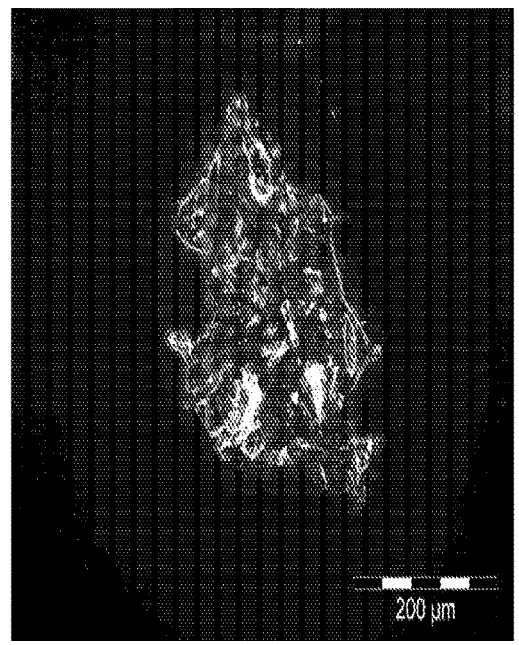

Spray dried powder, in contrast is spherical and glassy (FIGS. 9C and 10C).

The crystal size for refractive window or freeze dried powder is approximately 7 times larger than spray dried powder produced from the same purified grape pigments. Ninety percent of the refractive window and freeze dried powder crystals were less than 277-287 μm whereas 90 percent of the spray dried particles are less than 38 μm in diameter. As a result of their larger average particle size, the crystalline powders produced by refractive window and freeze drying exhibit less dust in handling when compared to an equivalent spray dried powder, which results in less airborne product loss and cleaner and safer use in a manufacturing environment.

The particle density for refractive window and freeze dried powder is 50 percent greater than the value for spray dried powder: 1.5 versus 0.9 grams/cm$^3$.

Table 3 summarizes the powder flowability characteristics for purified grape anthocyanin pigments dried using refractive window and spray drying processes. As shown, purified powder produced using refractive window drying is less cohesive and exhibits lower wall friction and higher air permeability compared to the spray dried version. These properties result in smaller hopper outlet requirements, less steep hopper angle requirements, and higher steady state discharge flow rates respectively.

TABLE 3

Flowability Characteristics for Purified Grape Pigments

| Parameter | Unit of Measure | Drying Method | |
|---|---|---|---|
| | | Refractive Window | Spray |
| Cohesive Arch in Mass Flow Bin[1] | | | |
| Continuous Flow | cm | 9 | 55 |
| Continuous Flow after 1 day at rest | cm | 12 | 73 |
| Wall Friction[2] | | | |
| Continuous Flow | Angle | 18 | 11 |
| Continuous Flow after 1 day at rest | Angle | 18 | 11 |
| Permeability[3] | | | |
| Steady State Flow with 2 foot diameter opening | kg/min | 700 | 8 |

[1]Cohesive arch is the smallest outlet diameter to avoid arching in a mass flow bin. Smaller arch sizes allow higher throughput at the same outlet size and more design flexibility.
[2]Wall friction is the maximum mass flow angle needed to maintain steady flow. Larger angles allow more design flexibility.
[3]Permeability measures the critical mass flow rate that can be sustained without plugging.

Cohesive strength measures a powder's tendency to form ratholes and cohesive arches. Cohesive arch measurements determine the smallest hopper outlet size required to sustain steady-state flow without plugging. A smaller minimum outlet diameter is preferred since it requires smaller transfer pipe and mixing equipment. Purified grape pigment powder produced using refractive window drying can sustain steady flow in a cone-shaped outlet as small as 9 cm in diameter. The same purified pigment produced using a spray dryer requires a cone diameter as large as 55 cm to sustain steady-state flow, nearly 6 times larger.

Wall friction angle is another measure of a powder's resistance to hopper discharge or pipe flow and susceptibility to plugging. Larger angles indicate superior flowability because mass flow can occur with hopper walls farther from vertical orientation, thereby reducing the space footprint required to achieve a given flow rate. Purified powder produced using refractive window drying has a conical hopper wall friction angle of 18 degrees compared to 11 degrees for purified powder produced using spray drying and subject to the same outlet size, wall material and surface finish.

Powder permeability correlates with steady-state flow characteristics, with higher permeability able to sustain steady flow. Powders with high air permeability retain their form and sustain high flow rates through confined openings while powders with low permeability experience discharge rate limitations due to interaction with air. Flowability characteristics are quantified by determining the steady-state flow of a powder through a fixed opening. Purified powder produced using refractive window drying can sustain steady state flow close to 700 kg/min through a 2-foot diameter conical opening compared to only 8 kg/min for purified powder produced using spray drying. Similar enhanced flowability characteristics as described above for purified grape pigments are expected to hold true for other purified natural pigments purified using the same purification process and dried using freeze drying.

In embodiments, the pigment or colorant are formulated as a composition. The pigments or colorant may be formulated as an aqueous solution, emulsion, suspension, and/or dispersion. The pigments or pigment compositions are contemplated for any suitable situation of adding or enhancing color. In embodiments, the pigment or pigment compositions are used in food, drugs, and/or cosmetic applications.

EXAMPLES

The following example is illustrative in nature and is in no way intended to be limiting.

Example 1

Crystalline Colorant Formation

A red grape juice concentrate and a purple carrot juice concentrate were separately reconstituted to about 18-22° Brix The red grape juice concentrate and purple carrot juice concentrate were separately purified through ultrafiltration and diafiltration across a PES membrane system.

Purified red grape juice concentrate and purple carrot juice concentrate were separately concentrated using a falling film evaporator and then dried using a refractive window dryer. Purification data was measured and the results are shown in Table 5.

TABLE 5

Crystal Purification Data

| | Product | Sugars (Total) | Fructose | Glucose | Sucrose | Moisture | Color (520 nm) | Sugars on dry basis | Color Strength on Dry Basis |
|---|---|---|---|---|---|---|---|---|---|
| Grape | Red Grape Juice Concentrate | 59.7 | 30.6 | 29.1 | 0 | 36.96 | 1,994 | 94.7 | 3,163 |
| Grape | Crystal Red Grape | 8.6 | 4.49 | 4.13 | 0 | 6.14 | 44,040 | 9.2 | 46,921 |
| Grape | Crystal Red Grape | 21.7 | 11.5 | 10.2 | 0 | 6.59 | 39,340 | 23.2 | 42,115 |
| Grape | Crystal Red Grape | 12.1 | 6.49 | 5.57 | 0 | 6.81 | 43,170 | 12.9 | 46,325 |
| Grape | Crystal Red Grape | 16.7 | 9.1 | 7.57 | 0 | 6.37 | 50,010 | 17.8 | 53,412 |
| Carrot | Purple Carrot Juice Concentrate | 46.2 | 4.56 | 5.95 | 35.69 | 35.69 | 9,089 | 71.8 | 14,133 |
| Carrot | Crystal Purple Carrot | 4.7 | 1.75 | 2.5 | 0.489 | 6.3 | 118,600 | 5.1 | 126,574 |
| Carrot | Crystal Purple Carrot | 16.3 | 3.72 | 5.09 | 7.5 | 6.2 | 88,080 | 17.4 | 93,902 |
| Carrot | Crystal Purple Carrot | 14.7 | 1.58 | 2.51 | 10.6 | 7.32 | 92,060 | 15.9 | 99,331 |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A system, comprising:
   a purifier device for purifying a juice of a plant containing pigments by removing at least a portion of non-pigment compounds from the juice to produce a liquid feed, wherein the purifying comprises at least one of ultrafiltration and diafiltration, adsorption/desorption chromatography, fermentation, a subcritical fluid extraction process, or a supercritical fluid extraction process;
   a conveyor belt having a top surface, wherein the conveyor belt is configured to receive the liquid feed on the top surface;
   an applicator tray at a first end of the conveyor belt that receives the liquid feed and provides the liquid feed to the top surface; and
   one or more heating trays underneath the conveyor belt that heat the liquid feed to facilitate production of a crystalline product from the liquid feed, wherein hot water at a temperature of up to about 210° F. circulates through the one or more heating trays.

2. The system of claim 1, further comprising an air pump and a feed barrel connected to the air pump via a suction hose.

3. The system of claim 2, wherein the air pump pumps the liquid feed from the feed barrel into a feed balance tank.

4. The system of claim 3, wherein the air pump is controlled by a level of the liquid feed in the feed balance tank.

5. The system of claim 1, further comprising valves on one or more feed spouts that drain the liquid feed onto the applicator tray, forming a thin layer of the liquid feed on the moving surface of the belt.

6. The system of claim 1, further comprising a tunnel through which the conveyor belt passes.

7. The system of claim 1, wherein the liquid feed has a temperature that is lower than the temperature of the hot water.

8. The system of claim 1, further comprising air blowers that move water vapors away from the conveyor belt.

9. The system of claim 1, further comprising a plastic edge to facilitate removing the crystalline product from the conveyor belt.

10. The system of claim 1, wherein the liquid feed includes a pigment selected from the group consisting of anthocyanins, carotenoids, betalains, curcumin, carminic acid, carminic acid derivatives, chlorophyll, and chlorophyll derivatives.

11. The system of claim 1, further comprising a heat exchanger.

12. The system of claim 1, wherein the purifier device comprises a polymeric membrane system, and wherein the purifying comprises performing the ultrafiltration and diafiltration across the polymeric membrane system.

13. The system of claim 1, further comprising a mill for milling the crystalline product.

14. The system of claim 1, wherein the conveyor belt is made of plastic.

\* \* \* \* \*